(12) United States Patent
Yonemitsu et al.

(10) Patent No.: US 9,404,083 B2
(45) Date of Patent: Aug. 2, 2016

(54) METHOD FOR AMPLIFYING NK CELLS

(75) Inventors: Yoshikazu Yonemitsu, Fukuoka (JP); Yui Harada, Fukuoka (JP); Satoru Saito, Fukuoka (JP); Yuichiro Yazaki, Minato-ku (JP); Masato Okamoto, Minato-ku (JP); Takefumi Ishidao, Minato-ku (JP)

(73) Assignees: KYUSHU UNIVERSITY, NATIONAL UNIVERSITY CORPORATION, Fukuoka (JP); TELLA, INC., Tokyo (JP)

( * ) Notice: Subject to any disclaimer, the term of this patent is extended or adjusted under 35 U.S.C. 154(b) by 113 days.

(21) Appl. No.: 14/129,143

(22) PCT Filed: Jun. 20, 2012

(86) PCT No.: PCT/JP2012/065718
§ 371 (c)(1),
(2), (4) Date: Dec. 24, 2013

(87) PCT Pub. No.: WO2012/176796
PCT Pub. Date: Dec. 27, 2012

(65) Prior Publication Data
US 2014/0120072 A1 May 1, 2014

(30) Foreign Application Priority Data
Jun. 24, 2011 (JP) .................................. 2011-140725
Feb. 3, 2012 (JP) .................................. 2012-021972

(51) Int. Cl.
A61K 35/28 (2015.01)
A61K 38/00 (2006.01)
C12N 5/0783 (2010.01)
A61K 35/17 (2015.01)

(52) U.S. Cl.
CPC .............. *C12N 5/0646* (2013.01); *A61K 35/17* (2013.01); *C12N 2501/2302* (2013.01)

(58) Field of Classification Search
None
See application file for complete search history.

(56) References Cited

U.S. PATENT DOCUMENTS

| | | | | |
|---|---|---|---|---|
| 8,877,182 B2 * | 11/2014 | Alici | ..................... | C12N 5/0646 424/93.71 |
| 2003/0068306 A1 * | 4/2003 | Dilber | .................. | C12N 5/0646 424/93.7 |
| 2004/0019390 A1 | 1/2004 | Velardi | | |
| 2006/0093605 A1 | 5/2006 | Campana et al. | | |
| 2009/0068141 A1 | 3/2009 | Parkhurst et al. | | |
| 2009/0257991 A1 | 10/2009 | Li et al. | | |
| 2013/0157364 A1 | 6/2013 | Hong et al. | | |

FOREIGN PATENT DOCUMENTS

| | | |
|---|---|---|
| JP | 2007-297291 A | 11/2007 |
| JP | 2011-517944 A | 6/2011 |
| JP | 2011-239701 A | 12/2011 |
| JP | 2013-6793 A | 1/2013 |
| KR | 10-1039843 B1 | 6/2011 |
| WO | 2004056392 A1 | 7/2004 |
| WO | 2006050270 A2 | 5/2006 |
| WO | WO 2007/103901 A2 | 9/2007 |
| WO | 2008023874 A1 | 2/2008 |
| WO | WO 2008/153150 A1 | 12/2008 |
| WO | 2009045360 A2 | 4/2009 |
| WO | WO 2010/013947 A2 | 2/2010 |
| WO | 2010110734 A1 | 9/2010 |
| WO | WO 2011/030851 A1 | 3/2011 |
| WO | 2011080740 A1 | 7/2011 |

OTHER PUBLICATIONS

Carlens et al., Human Immunol, 2001, v.62, pp. 1092-1098.*
International Search Report (PCT/ISA/210) mailed on Sep. 25, 2012, by the Japanese Patent Office as the International Searching Authority for International Application No. PCT/JP2012/065718.
International Search Opinion (PCT/IPEA/409) mailed on Jun. 11, 2013, by the Japanese Patent Office as the International Searching Authority for International Application No. PCT/JP2012/065718.
Office Action received in the corresponding Japanese patent application on Nov. 26, 2013 and a partial translations.
Kohjin Bio Co., Ltd., Internet Web Site and English Abstract, Jul. 28, 2010, 7 pages.
Male et al., "Immature NK Cells, Capable of Producing IL-22, Are Present in Human Uterine Mucosa", Journal of Immunology, 2010, vol. 185, No. 7, pp. 3913-3918.
Miller et al., "Blood—Successful adoptive transer and in vivo expansion of human haploidentical NK cells in patients with cancer", 105; 3051, 2005, pp. 3050-3057.
Rubnitz et al., "NKAML: A Pilot Study to Determine the safety and Feasibility of Haploidentical Nature Killer Cell Transplantation in Childhood Acute Myeloid Leukemia", Journal of Clinical Oncology, 28: 955, 2010, pp. 955-959.
Cho et al., "Expansion and Activation of Natural Killer Cells for Cancer Immunotherapy", Korean J Lab Med, 29: 89, 2009, pp. 89-96.
Carlens et al., "A New Method for In Vitro Expansion of Cytotoxic Human CD3⁻-CD59⁺ Natural Killer Cells", Human Immunology 62: 1092, 2001, pp. 1092-1098.

(Continued)

*Primary Examiner* — Michail Belyavskyi
(74) *Attorney, Agent, or Firm* — Buchanan, Ingersoll & Rooney PC

(57) ABSTRACT

A technique is needed which can amplify NK cells in vitro and prepare optimum number of NK cells for the adoptive immunotherapy.
A method for amplifying NK cells is provided which comprises steps of: preparing cell population which is comprised of NK cells, removing T cells from the cell population which is comprised of NK cells, and, after removal of T cells, cultivating the remaining cells in a medium supplemented with 2500 to 2831 IU/mL of IL-2. The method for amplifying NK cells of the present invention may comprise a step of removing hematopoietic progenitor cells from the cell population. The present invention provides a pharmaceutical composition for adoptive immunotherapy, comprising NK cells which are prepared by the amplifying method of the present invention.

18 Claims, 13 Drawing Sheets

(56) References Cited

OTHER PUBLICATIONS

Alici et al., "Blood—Autologous antitumor activity by NK cells expanded from myeloma patients using GMP-compliant components", 111: 3155, 2008, pp. 3154-3162.

Fujisaki et al., "Expansion of Highly Cytotoxic Human Natural Killer Cells for Canvcer Cell Therapy", Cancer Research, 69:4010, 2009, pp. 4009-4017.

Satoru Saito et al. "Ex Vivo Generation of Highly Purified and Activated Natural Killer Cells from Human Peripheral Blood", Human Gene Therapy methods, vol. 24, No. 4, Aug. 1, 2013, pp. 241-252.

Extended Search Report issued on Dec. 4, 2014 by the European Patent Office, in corresponding European Patent Application No. 12801859.5. (11 pages).

Office Action (Notice of Grounds for Rejection) issued on Mar. 4, 2014, by the Japanese Patent Office in corresponding Japanese Patent Application No. 2012-021972 and partial English translation of the Office Action. (4 pages).

Dewan, et al.: "Role of natural killer cells in hormone-independent rapid tumor formation and spontaneous metastasis of breast cancer cells in vivo," Breast Cancer Res. Treat., (2007), 104, pp. 267-275.

Office Action issued by the Japanese Patent Office in corresponding Japanese Patent Application No. 2014-011951 on Jan. 18, 2016 (4 pages).

\* cited by examiner

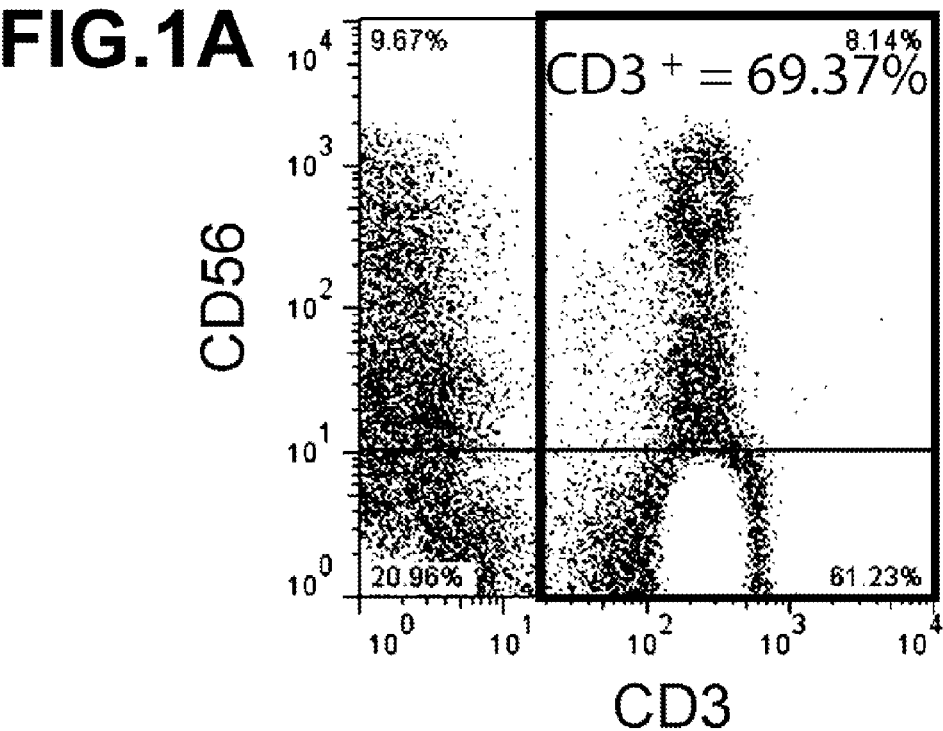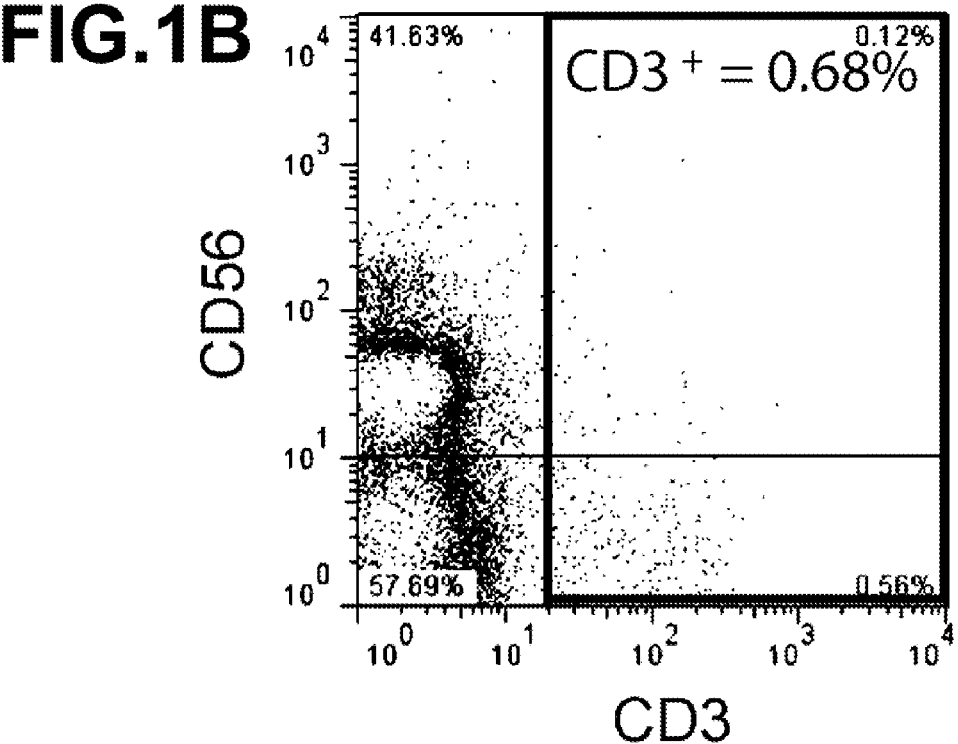

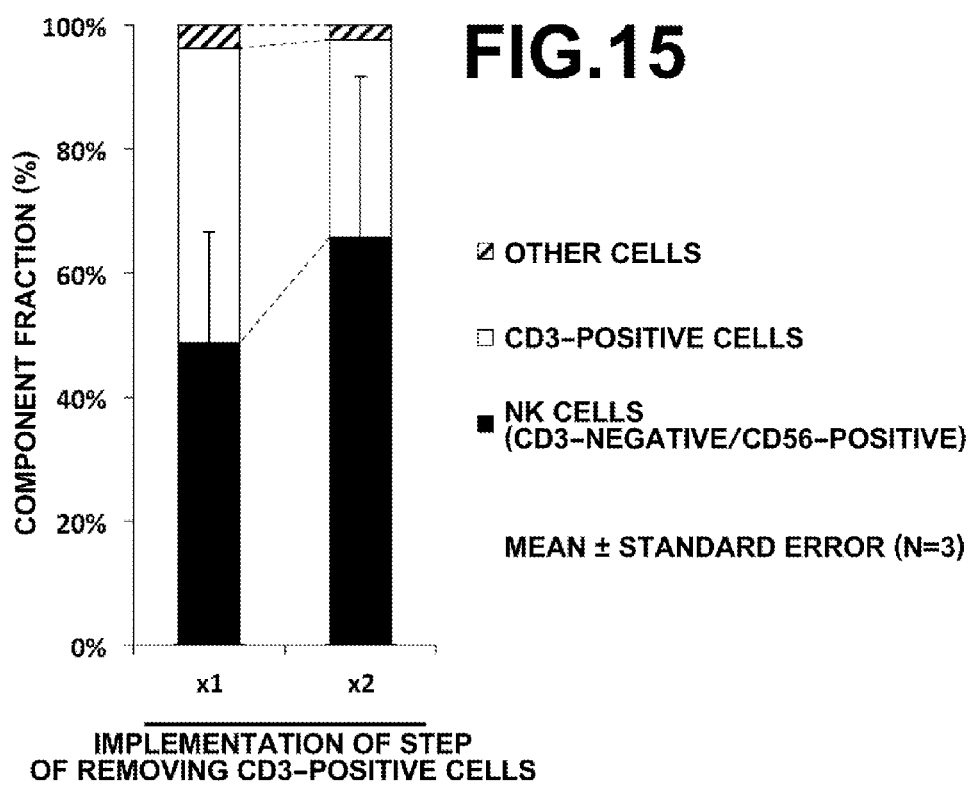

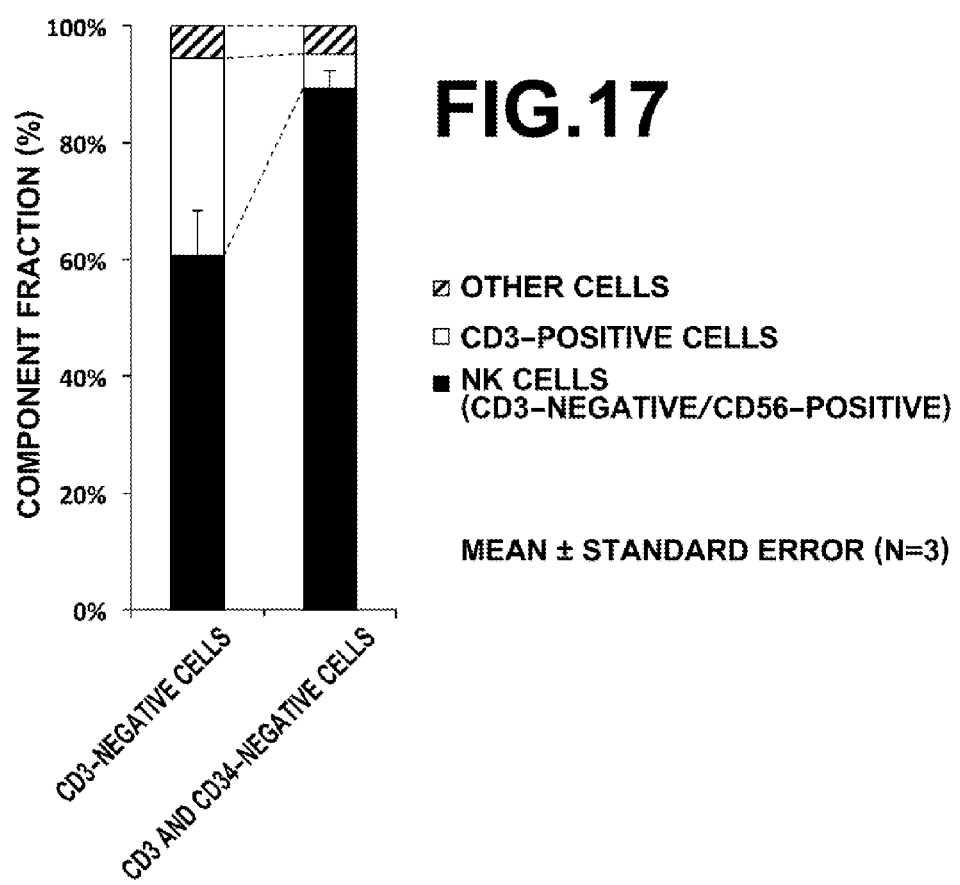

METHOD FOR AMPLIFYING NK CELLS

FIELD OF THE INVENTION

The present invention relates to a method for amplifying natural killer (NK) cells which are highly amplified and purified and have a high cytolytic activity. The present invention also relates to a pharmaceutical composition comprising the NK cells obtained by the method.

DESCRIPTION OF THE RELATED ART

NK cells do not attack normal cells which express MHC class I molecules, but mainly attack cells with reduced or lacking expression of MHC class I molecules. Adoptive immunotherapy with allotype NK cells for malignancies and infectious diseases has the technical merit of circumventing the adverse effect of Graft-versus-Host (GVH) disease. In fact, according to reports by Millers et al. (Non-patent Document 1: Blood, 105:3051 (2005)) and by Rubnitz et al. (Non-patent Document 2: J. Clin. Oncol., 28:955 (2010)), when cancer patients as recipients were implanted with concentrated NK cells from fresh peripheral blood mononuclear cells of donors who were close relatives of the recipients, the implanted NK cells transiently survived in the recipients and maintained cytolytic activity without manifesting adverse effects to the recipients. However, there have not been any reports of clinical trials demonstrating the efficacy of adoptive immunotherapy of NK cells. One of the reasons is because it is impossible to keep the population of NK cells large enough to kill target cells, such as malignant cells or pathogen-infected cells, in the recipients until the target cells are killed, due to the limit of the number of cells capable of being collected from a donor by lymphocyte apheresis.

A round of apheresis of healthy adult peripheral blood can yield about $1 \times 10^{10}$ mononuclear cells. Given the composition of NK cells in peripheral blood mononuclear cells as about 7%, $7 \times 10^8$ NK cells are expected (Non-patent Document 3: Cho, D. and Campana, D., Korean J. Lab. Med., 29:89 (2009)). On the other hand, for a NK cell transplantation, it is necessary to use NK cells in the order of $1 \times 10^5$ cells/kg to $2 \times 10^7$ cells/kg (Non-patent Document 1) or $5 \times 10^5$ cells/kg to $8.1 \times 10^7$ cells/kg (Non-patent Document 2). Assuming that a patient's body weight is 60 kg, $6 \times 10^6$ cells to $4.8 \times 10^9$ cells of NK cells are required. These cells amount to 0.0086 to 6.86 times as many as the number of NK cells obtained from one round of apheresis of healthy adult peripheral blood. The duration of NK cell survival, however, is merely 2 to 189 days with a median of 10 days, and does not correlate with the number of NK cells administered according to Non-patent Document 2, for example. This means that, in order to keep a sufficient number of NK cells to kill target cells such as malignant cells and pathogen-infected cells completely in the recipient body until the target cells are completely killed, it is necessary to repeat NK cell transplantation frequently, which is a heavy burden to the patient.

Methods are under development by which NK cells collected from a donor is first amplified in vitro to obtain a sufficient number of NK cells to kill the target cells completely. Terunuma, H. et al. (Patent Document 1: Japanese Published Patent Application No. 2007-297292) cultivated healthy peripheral blood mononuclear cells for 13 days in the presence of OKT3, an agonist antibody against human CD3, IL-2 and anti-CD16 antibody, and amplified NK cells 130 fold with a purity of 81.2%. The cytotoxic potential of the NK cells against K562 cells (E:T=3:1) was 66%. Tanaka, J. et al. (Patent Document 2: Japanese Patent Application No. 2011-140504, corresponding to Japanese Published Patent Application No. 2013-6793), cultivated healthy peripheral blood mononuclear cells for 21 days in a medium supplemented with IL-2, IL-15, anti-CD3 antibody, 5% human AB serum, tacrolimus and dalteparin, and amplified NK cells 6268 fold with a purity of 73.4%. The cytotoxic activity of the NK cells against K562 cells (E:T=1:1) was about 55%. Carlens, S. et al. (Non-patent Document 4: Hum. Immunol., 62:1092 (2001)) reported that they cultivated healthy peripheral blood mononuclear cells for 21 days in the presence of OKT3, the agonist antibody against human CD3, and IL-2, to amplify NK cells 193 fold with a purity of 55%. The cytotoxic activity of the NK cells against K562 cells (E:T=1:1) was 45%. Alici, E. et al. (Non-patent Document 5: Blood, 111:3155 (2008)) reported that they cultivated peripheral blood mononuclear cells from a myeloma patient for 20 days under similar conditions, to amplify NK cell 1625 fold with a purity of 65%. The cytotoxic activity of the NK cells against K562 cells (E:T=1:1) was about 10%. Fujisaki, H. et al. (Non-patent Document 6: Cancer Res., 69:4010 (2009)) reported that healthy peripheral blood mononuclear cells were cultivated for 21 days under a condition that leukemia cells which were genetically modified to express factors activating NK cells were used as feeder cells, to amplify NK cells 277 fold with a purity of 96.8%. The maximum cytotoxic activity of the NK cells against K562 cells (E:T=1:1) was about 90%.

The cytotoxic activities (E:T=1:1) of the NK cells amplified according to Terunuma, H. et al. (Patent Document 1), Tanaka, J. et al. (Patent Document 2), Carlens, S. et al. (Non-patent Document 4) and Alici, E. et al. (Non-patent Document 5) were 66%, about 55%, 45%, and about 10%, respectively. These conventional techniques, therefore, are not desirable, as the cytotoxic potential of the NK cells were too low to have a high therapeutic efficacy, and require more NK cells to be administered. The cytotoxic activity of NK cells amplified according to Fujisaki, H. et al. (Non-patent Document 6) was up to about 90%. Still their method is not desirable, because they used genetically modified malignant cells as feeder cells, which have a risk of contaminating the final product.

DISCLOSURE OF THE INVENTION

It is therefore necessary to develop a technique which can amplify NK cells with high cytotoxic activity and high purity from umbilical cord blood or peripheral blood without using any feeder cells.

The present invention provides a method for amplifying NK cells. The method of the present invention comprises the steps of: preparing a cell population which is comprised of NK cells, removing T cells from the cell population which is comprised of NK cells, and, after removal of T cells, cultivating the remaining cells in a medium supplemented with 2500 to 2831 IU/mL of IL-2.

In the method for amplifying NK cells of the present invention, the step of removing T cells may be implemented by a step of removing CD3-positive cells.

The method for amplifying NK cells of the present invention may comprise a step of removing hematopoietic progenitor cells from the cell population.

In the method for amplifying NK cells of the present invention, the step of removing hematopoietic progenitor cells from the cell population may be implemented by a step of removing CD34-positive cells.

In the method for amplifying NK cells of the present invention, the medium may comprise self serum of the donor, AB-type serum, and/or serum albumin.

In the method for amplifying NK cells of the present invention, the step of preparing cell population which is comprised of NK cells may be implemented by a step of separating mononuclear cells from blood cells collected from a subject.

In the method for amplifying NK cells of the present invention, the blood cells may be collected from peripheral blood, umbilical cord blood, bone marrow and/or a lymph node.

In the method for amplifying NK cells of the present invention, the blood cells may be collected from peripheral blood using apheresis.

In the method for amplifying NK cells of the present invention, the cell population may be prepared from at least one kind of cell selected from a group consisting of: hematopoietic stem cells derived from any stem cells selected from a group consisting embryonic stem cells, adult stem cells and induced pluripotent stem cells (iPS cells); hematopoietic stem cells derived from umbilical cord blood; hematopoietic stem cells derived from peripheral blood; hematopoietic stem cells derived from bone marrow blood; umbilical cord blood mononuclear cells; and peripheral blood mononuclear cells. The donor of the cell population may be the recipient, that is, the patient himself or herself, a blood relative of the patient, or a person who is not a blood relative of the patient. The NK cells may be derived from a donor whose major histocompatibility antigen complex (MHC) and killer immunoglobulin-like receptors (KIR) do not match with those of the recipient.

The present invention provides a pharmaceutical composition for adoptive immunotherapy, comprising NK cells which are prepared by the amplifying method of the present invention. The pharmaceutical composition of the present invention may comprise NK cell progenitors, T cells, NKT cells, hematopoietic progenitor cells or the like, in addition to the amplified NK cells.

The pharmaceutical composition of the present invention may be used for treating an infectious disease and/or a cancer.

The pharmaceutical composition of the present invention may be administered to a patient whose HLA genotype is different from the NK cells prepared by the amplifying method.

The present invention provides a method for adoptive immunotherapy comprising the steps of: preparing a cell population which is comprised of NK cells, removing T cells from the cell population, after removal of T cells, cultivating the remaining cells in a medium supplemented with 2500 to 2831 IU/mL of IL-2, and transplanting the NK cells which are amplified from the remaining cells to a patient. The method may comprise a step of removing hematopoietic progenitor cells from the cell population. In the step of transplanting the NK cells to the patient, the amplified NK cells may be transplanted together with NK cell progenitors, T cells, NKT cells, hematopoietic progenitor cells or the like. The method for adoptive immunotherapy of the present invention may be employed for treating and/or preventing an infectious disease and/or cancer. The method for adoptive immunotherapy of the present invention may comprise a step of transplanting the NK cells prepared by the amplifying method of the present invention to a patient whose HLA genotype is different from the genotype of the NK cells. In the method for adoptive immunotherapy of the present invention, the step of transplanting the NK cells to the patient may be implemented by a step of administering the pharmaceutical composition of the present invention to the patient.

In the method for adoptive immunotherapy of the present invention, the cell population which is comprised of NK cells may be prepared from at least one kind of cell selected from a group consisting of: hematopoietic stem cells derived from any stem cells selected from a group consisting embryonic stem cells, adult stem cells and induced pluripotent stem cells (iPS cells); hematopoietic stem cells derived from umbilical cord blood; hematopoietic stem cells derived from peripheral blood; hematopoietic stem cells derived from bone marrow blood; umbilical cord blood mononuclear cells; and peripheral blood mononuclear cells. The donor of the cell population which is comprised of NK cells may be the recipient, that is, the patient himself or herself, a blood relative of the patient, or a person who is not a blood relative of the patient. The NK cells may be derived from a donor whose major histocompatibility antigen complex (MHC) and killer immunoglobulin-like receptors (KIR) do not match with those of the recipient.

In this specification, "NK cells" are mononuclear cells which are CD3-negative and CD56-positive, and which have a cytotoxic activity against cells with reduced or lacking expression of MHC class I molecules.

In the amplifying method of the present invention, the cell population which is comprised of NK cells may be prepared using various procedures known to those skilled in the art. For example, to collect mononuclear cells from blood such as umbilical cord blood and peripheral blood, the buoyant density separation technique may be employed. NK cells may be collected with immunomagnetic beads. Furthermore, the NK cells may be isolated and identified using a FACS (fluorescent activated cell sorter) or a flow cytometer, following immunofluorescent staining with specific antibodies against cell surface markers. The NK cells may be prepared by separating and removing cells expressing cell surface antigens CD3 and/or CD34, with immunomagnetic beads comprising, but not limited to, Dynabeads (trade mark) manufactured by Dynal and sold by Invitrogen (now Life Technologies Corporation), and CliniMACS (trade mark) of Miltenyi Biotec GmbH. T cells and/or hematopoietic progenitor cells may be selectively injured or killed using specific binding partners for T cells and/or hematopoietic progenitor cells. The step of removing the T cells from the mononuclear cells may be a step of removing cells of other cell types, such as hematopoietic progenitor cells, B cells and/or NKT cells, together with the T cells. The step of removing the hematopoietic progenitor cells from the mononuclear cells may be a step of removing cells of other cell types, such as T cells, B cells and/or NKT cells, together with the hematopoietic progenitor cells.

In the amplifying method of the present invention, the mononuclear cells separated from the umbilical cord blood and peripheral blood may be cryopreserved and stored to be thawed in time for transplantation to the patient. Alternatively, the mononuclear cells may be frozen during or after amplification by the method for amplifying the NK cells of the present invention, and thawed in time for transplantation to the patient. Any method known to those skilled in the art may be employed in order to freeze and thaw the blood cells. Any commercially available cryopreservation fluid for cells may be used to freeze the cells.

In the method for adoptive immunotherapy of the present invention, a solution for suspending live NK cells, for example, saline, phosphate buffered saline (PBS), medium, serum and the like is generally used. The solution may comprise a carrier which is pharmaceutically acceptable as a pharmaceutical product or quasi-drug. The method for adoptive immunotherapy using NK cells of the present invention may be applied for treating and/or preventing various disease conditions which are affected by NK cells. The disease conditions include, but are not limited to, for example, oral cancer, gallbladder cancer, bile duct cancer, lung cancer, liver cancer, colorectal cancer, kidney cancer, bladder cancer, leukemia, and infectious diseases caused by viruses, microbes, or the like. The method for adoptive immunotherapy of the present invention may be carried out alone or in combination with surgery, chemotherapy, radiation therapy or the like. In the method for adoptive immunotherapy of the present invention, the NK cells may be transplanted by being administered, for example, intravenously, intra-arterially, subcutaneously, intraperitoneally, etc.

A cell culture medium for preparing the NK cells of the present invention may be comprised of, but not limited to, KBM501 (Kohjin Bio Co. Ltd.), CellGro SCGM (CellGenix GmbH, Iwai Chemicals Company), X-VIVO15 (Lonza, Ltd, Takara Bio, Inc.), IMDM, MEM, DMEM, RPMI-1640 or the like.

The above-mentioned medium may be supplemented with interleukin-2 (IL-2) at a concentration which can achieve the purpose of the present invention. The IL-2 concentration may be 2500 to 2813 IU/mL. The IL-2 preferably has a human amino acid sequence, and for safety reasons, is preferably produced by recombinant DNA technology.

In the present specification, the concentration of IL-2 may be indicated with Japanese reference units (JRU) and international units (IU). As one IU is equivalent to about 0.622 JRU, 1750 JRU/mL corresponds to about 2813 IU/mL.

The above-mentioned medium may be supplemented with self serum of the subject, human AB-type serum which is available from Bio Whittaker (trademark, Lonza, Ltd, Takara Bio, Inc.) or the like, or human serum albumin derived from donated blood available from the Japanese Red Cross Society. Preferably, the self serum and human AB-type serum is supplemented at a concentration of 1 to 10%. Preferably, the human serum albumin derived from donated blood is supplemented at a concentration of 1 to 10%. The subject may be healthy volunteers or patients suffering from the above-mentioned diseases.

The medium may be comprised of an appropriate protein, cytokine, antibody, compound or other ingredient, under conditions that do not undermine the effect on NK cell amplification. The cytokine may be interleukin 3 (IL-3), interleukin 7 (IL-7), interleukin 12 (IL-12), interleukin 15 (IL-15), interleukin 21 (IL-21), stem cell factor (SCF) and/or FMS-like tyrosine kinase 3 ligand (Flt3L). The above-mentioned IL-3, IL-7, IL-12, IL-15, IL-21, SCF and Flt3L preferably have human amino acid sequence, and for safety reasons, are preferably produced by recombinant DNA technology. Under the condition that required number of NK cells shall be obtained, the exchange of the above-mentioned medium may be carried out any time after starting cultivation, but preferably, every 3 to 5 days.

In the amplifying method of the present invention, a culture vessel is comprised of, but not limited to, a commercially available dish, flask, plate, and a multiwell plate. There is no restriction as to culture conditions, under the condition that does not undermine the effect on NK cell amplification. However, conditions of culturing at 37° C., in an atmosphere of 5% $CO_2$ saturated with water vapor are generally employed. As the purpose of the present invention is to prepare a large number of NK cells, longer cultivation time in the medium will generate more obtained NK cells, and thus is favorable. The duration of culture is not especially restricted, under the condition that amplifies NK cells to a required number of cells.

In the amplifying method of the present invention, the cell population comprising the NK cells may be composed of NK cell progenitors, T cells, NKT cells, hematopoietic progenitor cells and the others. After amplification, the NK cells as desired may be selected by, for example, the buoyant density separation technique, immunomagnetic beads, FACS, flow cytometry, or the like. For example, the NK cells may be separated from the cell population selectively with an anti-CD3 antibody, anti-CD16 antibody, anti-CD34 antibody, anti-CD56 antibody, anti-CD69 antibody, anti-CD94 antibody, anti-CD107a antibody, anti-KIR3DL1 antibody, anti-KIR3DL2 antibody, anti-KIR2DL3 antibody, anti-KIR2DL1 antibody, anti-KIR2DS1 antibody, anti-KIR2DL5 antibody, anti-NKp46 antibody, anti-NKp30 antibody, anti-NKG2D antibody, or the like. The above-mentioned antibody may be a monoclonal antibody, a polyclonal antibody or others. Selection of NK cells may be carried out by selectively removing cells such as T cells, NKT cells, hematopoietic progenitor cells, or the like.

It is preferable that the method of the present invention and the production of the pharmaceutical composition of the present invention are performed under the condition which conforms to the regulations for production control and quality control of pharmaceutical products and quasi-drugs (good manufacturing practice, GMP).

The cytotoxic activity or cytotoxic potential of the amplified NK cells may be evaluated by methods commonly known to those skilled in the art. The cytotoxic activity is generally evaluated by determining radioactivity or fluorescent intensity quantitatively, following incubation of the NK cells (effector cells) and target cells labeled with a radioactive substance, fluorescent dye, or the like. The target cell may be, but not limited to, K562 cells, acute myeloid leukemia cells, chronic myeloid leukemia cells. The amplified NK cells may be characterized by RT-PCR, solid phase hybridization, ELISA, western blotting, immunoprecipitation, turbidimetric immunoassay, FACS, flow cytometry and other techniques.

In the present invention, whole blood collection of umbilical cord blood and peripheral blood, preparation of self serum, preparation of mononuclear cells from the whole blood, cell counts before and after cultivating the mononuclear cells, determination of component fractions of NK cells, T cells, hematopoietic progenitor cells and cells of other cell types contained in the mononuclear cells before and after cultivation, calculation of multiplicity of amplification, static analysis on measurement error and significance may be carried out by any method commonly known by those skilled in the art.

All of the documents cited in this application are incorporated by reference in their entirety.

BRIEF DESCRIPTION OF THE DRAWINGS

FIG. 1A is a flow cytometry chart of mononuclear cells doubly stained with antibodies against CD3 and CD56 before removing CD3-positive cells.

FIG. 1B is a flow cytometry chart of mononuclear cells doubly stained with antibodies against CD3 and CD56 after removing CD3-positive cells.

FIG. 15 is a bar graph illustrating component fraction of NK cells (CD3-negative/CD56-positive) relative to total cultured cells after removing CD3-positive cells once and twice.

FIG. 17 is a bar graph illustrating component fractions of NK cells (CD3-negative/CD56-positive) relative to total cultured cells amplified from CD3-negative cells and CD3- and CD34-negative cells.

BEST MODE FOR CARRYING OUT THE INVENTION

Figure 2A:
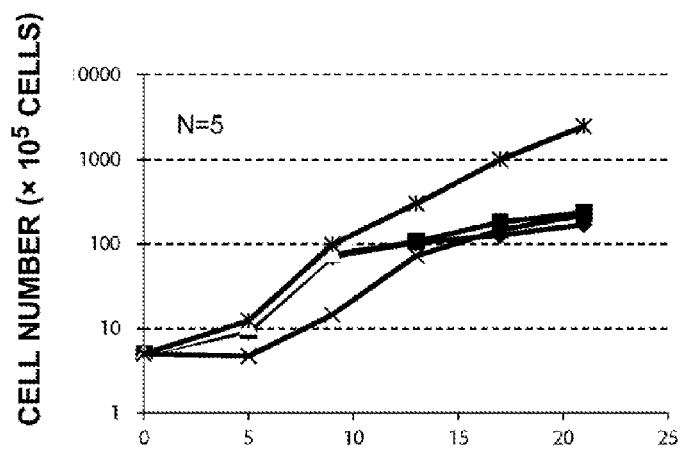
FIG. 2A is a graph illustrating individual growth curves of CD3-negative cells separated from mononuclear cells derived from peripheral blood of five healthy volunteers, as counted by the number of cells.

The examples described below are only for the purpose of illustration, and not intended to limit the scope of the present invention. The scope of the present invention is limited only by the language of the claims. It is understood that modifications to the present invention, for example, addition, deletion, and replacement of a feature of the present invention, may be carried out without departing from the spirit of the present invention.

EXAMPLES

Example 1

Amplification of NK cells (1)
1. Materials and Methods
(1) Collection of Peripheral Blood Peripheral blood was collected from healthy volunteers and patients with advanced cancer (oral cancer, gall bladder cancer and bile duct cancer). Experiments were performed under the authorization of the Research Ethics Committee of Departments in Medical Facilities of Kyushu University (Authorization Number: 22-176, Authorization Date: Mar. 31, 2011). Informed consents were obtained from the healthy volunteers and patients. Blood collection, cryopreservation and defrosting were carried out by methods commonly known by those skilled in the art.

(2) Separation of Mononuclear Cells from Peripheral Blood

The collected blood was diluted twice with a diluent (PBS supplemented with 1 mM of EDTA and 2% bovine calf serum (BSA)) kept at room temperature. 20 to 35 mL of the diluted blood was dispensed in centrifuge tubes and overlaid onto 10 to 15 mL of Ficoll Paque (trade mark, density: 1.077). The tubes were centrifuged at 500×g, for 20 minutes at room temperature, stopped without braking. All but a few mL of supernatant (blood plasma portion) was removed and an intermediate layer was recovered. The intermediate layer recovered from a one or two tubes was pooled in a new tube and its volume was adjusted to 50 mL using the diluent. A second round of centrifugation was carried out at 500×g, at room temperature, for 5 or 15 minutes. The supernatant was removed and the pellet was suspended in 30 mL of the diluent. A third round of centrifugation was carried out at 280×g, at room temperature, for 10 minutes. The supernatant was removed and the pellet was suspended in PBS supplemented with 2 mM of EDTA and 0.1% of BSA (referred to as "mononuclear cell suspension") at $1 \times 10^7$ cells/mL.

(3) Removal of CD3-Positive Cells

Magnetic beads, on which an anti-CD3 antibody (Dynabeads (trade mark) CD3) is immobilized, were rinsed once with PBS supplemented with 0.1% of BSA, and added to the mononuclear cell suspension at 50 uL per $10^7$ cells. The mononuclear cell suspension comprising the beads was mixed at 4° C. for 30 minutes with a rotator. Then, the magnetic beads were separated from the suspension with a magnet and the cells expressing CD3 on their cell surface (CD3-positive cells) were removed.

(4) Cultivation of Cell Population from which CD3-Positive Cells were Removed

The remaining cells in the suspension (referred to as "CD3-negative cells") were diluted with a cell culture medium (KBM501, 16025015, Kohjin Bio Co. Ltd., comprising 1750 JRU/mL of IL-2) supplemented with 5% self serum (referred to as "KBM medium") at $5 \times 10^5$ cells/mL, and inoculated on a six-well culture plate (140675, nunc, Thermo Fisher Scientific K.K.). Cells were cultivated at 37° C. for 21 days, in an atmosphere of 5% $CO_2$ saturated with water vapor. The medium was exchanged on Day 5, Day 9, Day 13 and Day 17. The cells were cultivated free of feeder cells.

(5) Analysis of Number of Cells and Cell Surface Markers

The cell number of the peripheral blood mononuclear cells was determined by counting the number of live cells between Days 0 and 21 with a hemocytometer. Cell surface markers of these cells were analyzed by flow cytometry with the following antibodies: anti-CD3 antibody (317308, BioLegend Japan KK), anti-CD16 antibody (556618, BD Pharmingen, Nippon Becton Dickinson Company, Ltd.), anti-CD56 antibody (304607, 318321, BioLegend Japan KK), anti-CD69 antibody (310905, BioLegend Japan KK), anti-KIR3DL1/KIR3DL2 antibody (130-095-205, Miltenyi Biotec K.K.), anti-KIR2DL3 antibody (FAB2014P, R&D SYSTEMS, COSMO BIO CO., LTD.), anti-KIR2DL1/KIR2DS1 antibody (339505, BioLegend Japan KK), anti-KIR2DL5 antibody (341303, BioLegend Japan KK), anti-NKp46 antibody (331907, BioLegend Japan KK), anti-NKp30 antibody (325207, BioLegend Japan KK), and anti-NKG2D antibody (320805, BioLegend Japan KK).

2. Results (1) Amplification of NK Cells of Healthy Volunteers

FIG. 1A is a flow cytometry chart of mononuclear cells doubly stained with antibodies against CD3 and CD56 before removing CD3-positive cells. FIG. 1B is a flow cytometry chart of mononuclear cells doubly stained with antibodies against CD3 and CD56 after removing CD3-positive cells. "CD3+=" represents component fraction of CD3-positive cells, that is, a percentage ratio of CD3-positive cells relative to the entire cultured cells. The component fraction of CD3-positive cells (%) was 69.37% before removing CD3-positive cells, and 0.68% after removing CD3-positive cells. As clearly shown by these results, CD3-positive cells were significantly depleted from the mononuclear cell suspension.

Figure 2B:
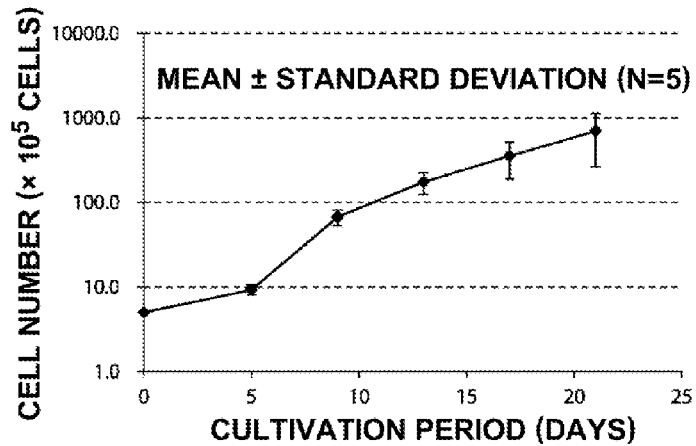
FIG. 2B is a graph illustrating an average growth curve of CD3-negative cells separated from mononuclear cells derived from peripheral blood of five healthy volunteers, as counted by the number of cells.

FIG. 2A is a graph illustrating individual growth curves of CD3-negative cells separated from mononuclear cells derived from peripheral blood of five healthy volunteers, as counted by cell number. FIG. 2B is a graph illustrating an average growth curve of CD3-negative cells separated from mononuclear cells derived from peripheral blood of five healthy volunteers, as counted by cell number. The number of CD3-negative cells per one mL of peripheral blood collected from five healthy volunteers was determined at the start of cultivation and after cultivation for 5, 9, 13, 17 and 21 days. The standard error of each experimental condition was calculated from the number of cells of the five experiments carried out under identical conditions. CD3-negative cells continuously increased from the start of cultivation until Day 21. The rate of growth kept fast until Day 13, and slowed down thereafter. CD3-negative cells increased from about $5 \times 10^5$ cells at the start of cultivation to about $700 \times 10^5$ cells on Day 21.

Figure 3A:
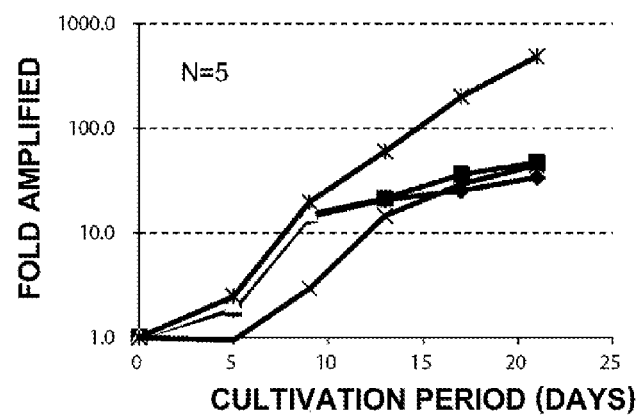
FIG. 3A is a graph illustrating individual growth curves of CD3-negative cells separated from mononuclear cells derived from peripheral blood of five healthy volunteers, as calculated in multiplicity of amplification.
Figure 3B:
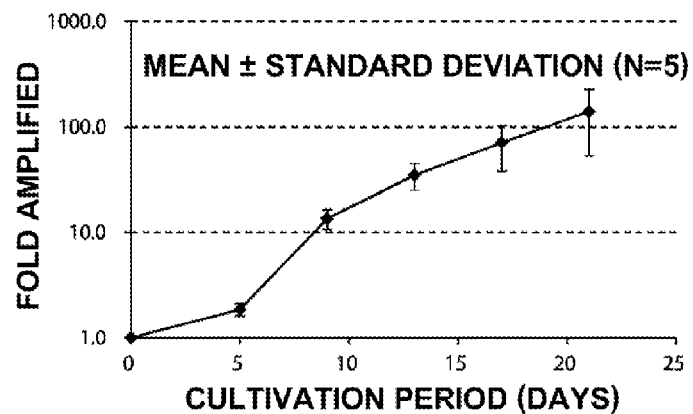
FIG. 3B is a graph illustrating an average growth curve of CD3-negative cells separated from mononuclear cells derived from peripheral blood of five healthy volunteers, as calculated in multiplicity of amplification.

FIG. 3A is a graph illustrating individual growth curves of CD3-negative cells separated from mononuclear cells derived from peripheral blood of five healthy volunteers, as calculated in multiplicity of amplification. FIG. 3B is a graph illustrating an average growth curve of CD3-negative cells separated from mononuclear cells derived from peripheral blood of five healthy volunteers, as calculated in multiplicity of amplification. The multiplicity of amplification was calculated by dividing the number of cells on Days 5, 6, 13, 17 and 21 by cell number at the start of cultivation. The standard error of each experimental condition was calculated from the number of cells of the five experiments carried out under identical conditions. The multiplicity of amplification of CD3-negative cells continuously increased from the start of cultivation to Day 21. The multiplicity of amplification kept increasing remarkably until Day 13 and reached at about 150 fold on Day 21.

Figure 4A:
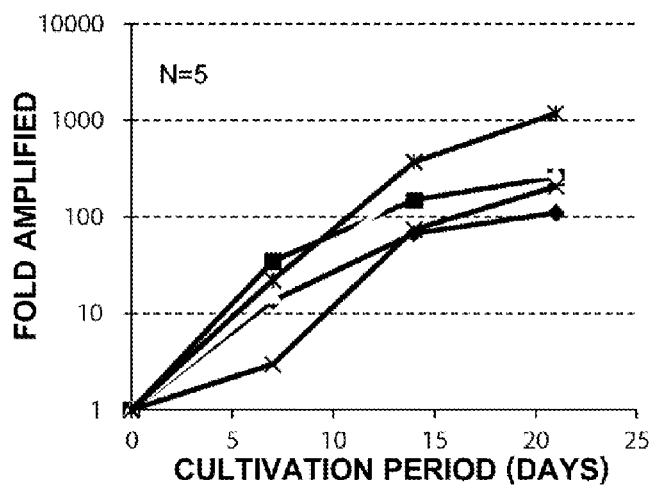
FIG. 4A is a graph illustrating individual growth curves of NK cells (CD3-negative/CD56-positive) separated from mononuclear cells derived from peripheral blood of five healthy volunteers, as calculated in multiplicity of amplification.
Figure 4B:
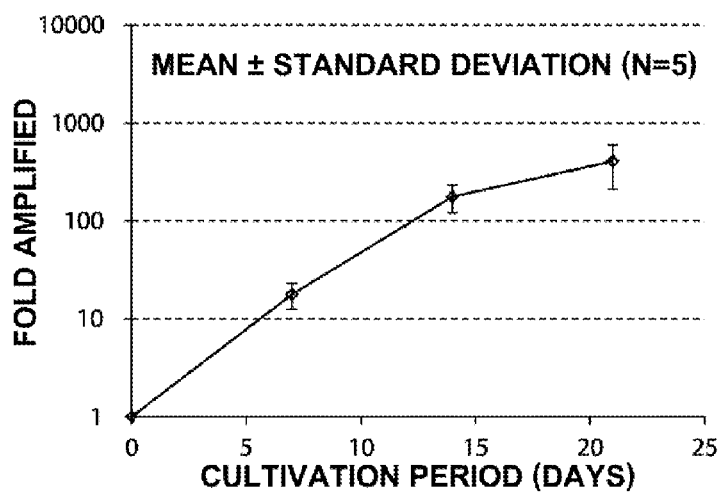
FIG. 4B is a graph illustrating an average growth curve of NK cells (CD3-negative/CD56-positive) separated from mononuclear cells derived from peripheral blood of five healthy volunteers, as calculated in multiplicity of amplification.

FIG. 4A is a graph illustrating individual growth curves of NK cells (CD3-negative/CD56-positive) separated from mononuclear cells derived from peripheral blood of five healthy volunteers, as calculated in multiplicity of amplification. FIG. 4B is a graph illustrating average growth curve of NK cells (CD3-negative/CD56-positive) separated from mononuclear cells derived from peripheral blood of five healthy volunteers, as calculated in multiplicity of amplification. In FIGS. 4A and 4B, CD3-negative cells were analyzed by flow cytometry after doubly stained with antibodies against CD3 and CD56. The multiplicity of amplification was calculated by dividing the number of NK cells on Days 7, 14 and 21 by the number of NK cells at the start of cultivation. The standard error of each experimental condition was calculated from the number of cells of the five experiments carried out under identical conditions. The multiplicity of amplification of NK cells kept increasing from the start of cultivation to Day 21. The multiplicity of amplification kept increasing remarkably until Day 14 and reached at about 400 fold on Day 21.

Figure 5A:
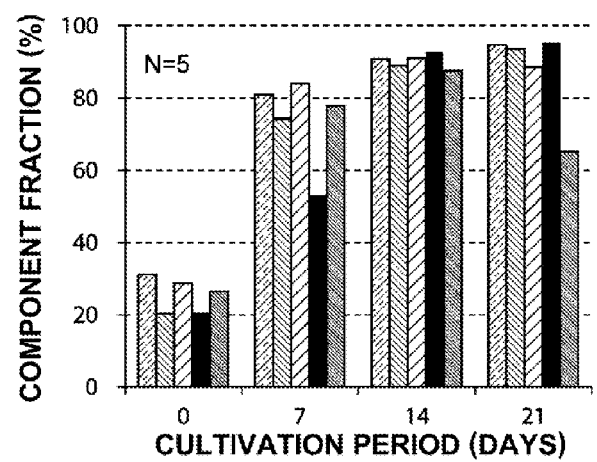
FIG. 5A is a graph illustrating temporal change of individual component fractions of NK cells (CD3-negative/CD56-positive) separated from five healthy volunteers, as determined by flow cytometry relative to total cultured cells.
Figure 5B:
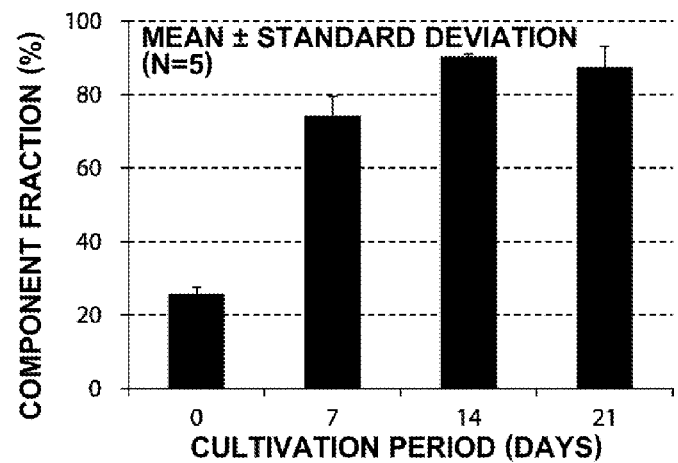
FIG. 5B is a graph illustrating temporal change of average component fraction of NK cells (CD3-negative/CD56-positive) separated from five healthy volunteers, as determined by flow cytometry relative to total cultured cells.

FIG. 5A is a graph illustrating temporal change of individual component fractions of NK cells (CD3-negative/CD56-positive) separated from five healthy volunteers, as determined by flow cytometry relative to total cultured cells. FIG. 5B is a graph illustrating temporal change of average component fraction of NK cells (CD3-negative/CD56-positive) separated from five healthy volunteers, as determined by flow cytometry relative to total cultured cells. In FIGS. 5A and 5B, CD3-negative cells were analyzed by flow cytometry after being doubly stained with antibodies against CD3 and CD56. "Component fraction of NK cells" represents a percentage ratio of NK cells relative to the entirety of cultured cells. The ordinate of the graph represents component fractions (%) of NK cells (CD3-negative/CD56-positive) relative to the entirety of cultured cells and the abscissa represents days of the cultivation period. The standard error of each experimental condition was calculated from the number of cells of the five experiments carried out under identical conditions. The component fraction of NK cells kept increasing from the start of cultivation to Day 21. The component fraction of NK cells kept increasing remarkably until Day 14 and reached approximately 90% on Day 14. It was shown that the present invention amplifies NK cells selectively over time.

(2) Amplification of NK Cells of Patients

Figure 6A:
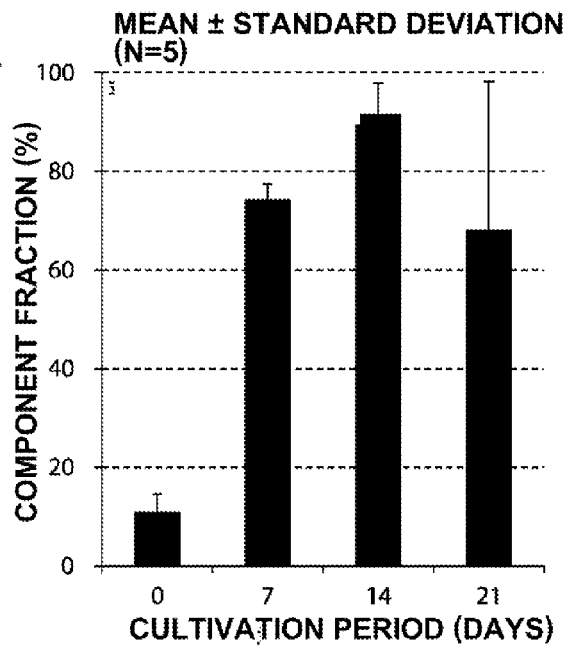
FIG. 6A is a graph illustrating temporal change of individual component fractions of NK cells (CD3-negative/CD56-positive) separated from patients with advanced cancer (oral cancer, gal bladder cancer and bile duct cancer), as determined by flow cytometry relative to total cultured cells.
Figure 6B:
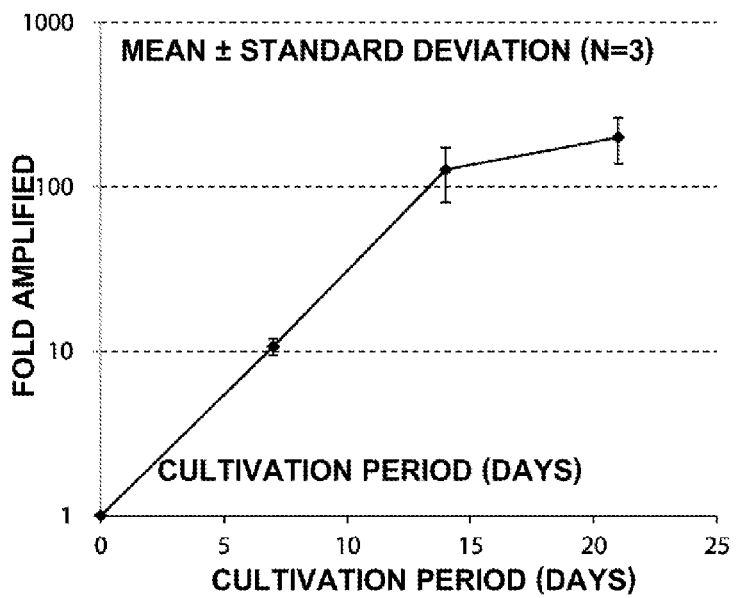
FIG. 6B is a graph illustrating an average growth curve of NK cells (CD3-negative/CD56-positive) separated from patients with advanced cancer (oral cancer, gal bladder cancer and bile duct cancer, as calculated in multiplicity of amplification.

FIG. 6A is a graph illustrating temporal change of individual component fractions of NK cells (CD3-negative/CD56-positive) separated from patients with advanced cancer (oral cancer, gall bladder cancer and bile duct cancer), as determined by flow cytometry relative to total cultured cells. FIG. 6B is a graph illustrating average growth curve of NK cells (CD3-negative/CD56-positive) separated from patients with advanced cancer (oral cancer, gall bladder cancer and bile duct cancer), as calculated in multiplicity of amplification. "Component fraction of NK cells" represents a percentage ratio of NK cells relative to the entirety of cultured cells. The ordinate of the graph of FIG. 6A represents component fractions (%) of NK cells (CD3-negative/CD56-positive) relative to entire cultured cells and the abscissa represents days of the cultivation period. The "multiplicity of amplification for NK cells" was calculated by dividing NK cell after amplification by NK cell number present in the peripheral blood mononuclear cells before amplification. The ordinate of the graph of FIG. 6B represents multiplicity of amplification of NK cells and the abscissa represents days of the cultivation period. The standard error of each experimental condition was calculated from the number of cells of the three experiments carried out under identical conditions. As illustrated in the graph of FIG. 6A, the component fraction of NK cells kept increasing remarkably until Day 14 and reached approximately 85% on Day 14. It was shown that the present invention amplifies NK cells selectively over time. As illustrated in the graph of FIG. 6B, the multiplicity of amplification of NK cells kept increasing from the start of cultivation to Day 14 and reached about 140 fold on Day 14. On Day 21, the component fraction of NK cells was decreased due to the growth of CD3-positive cells. However, the growth of NK cells was hardly affected by the growth of CD3-positive cells. From these results it was demonstrated that NK cells separated from patients of advanced cancer (oral cancer, gal bladder cancer and bile duct cancer) are amplified over time. It was also suggested that the present invention can amplify NK cells separated from patients of cancer, infectious diseases, or the like over time.

(3) Expression of Differentiation Markers of NK Cells

Figure 7:
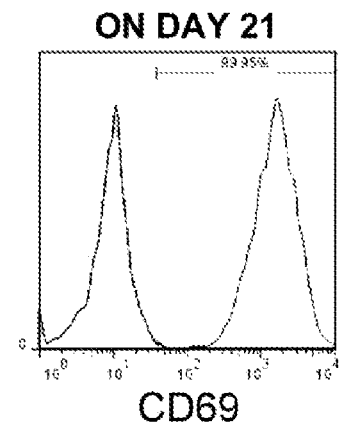
FIG. 7 is a flow cytometry chart comparing results of CD69 analysis.
Figure 8:
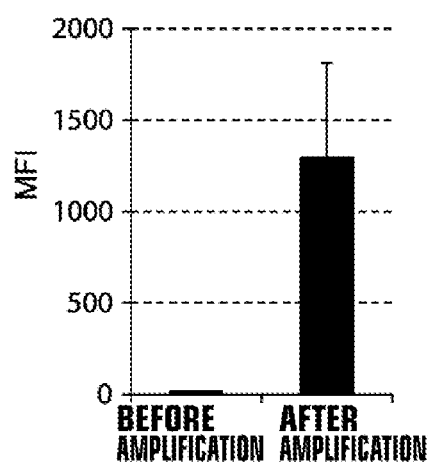
FIG. 8 is a graph comparing mean fluorescent intensity (MFI) values of flow cytometry with CD69.
Figure 9:
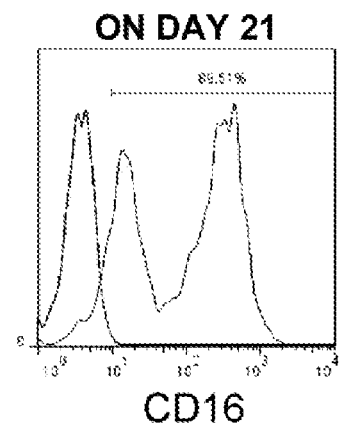
FIG. 9 is a flow cytometry chart comparing results of CD16 analysis.
Figure 10:
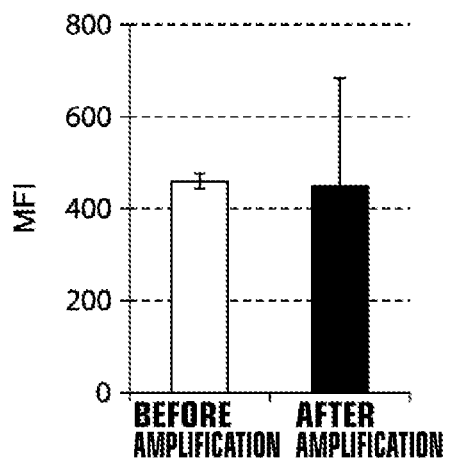
FIG. 10 is a graph comparing mean fluorescent intensity (MFI) values of flow cytometry with CD16.
Figure 11:
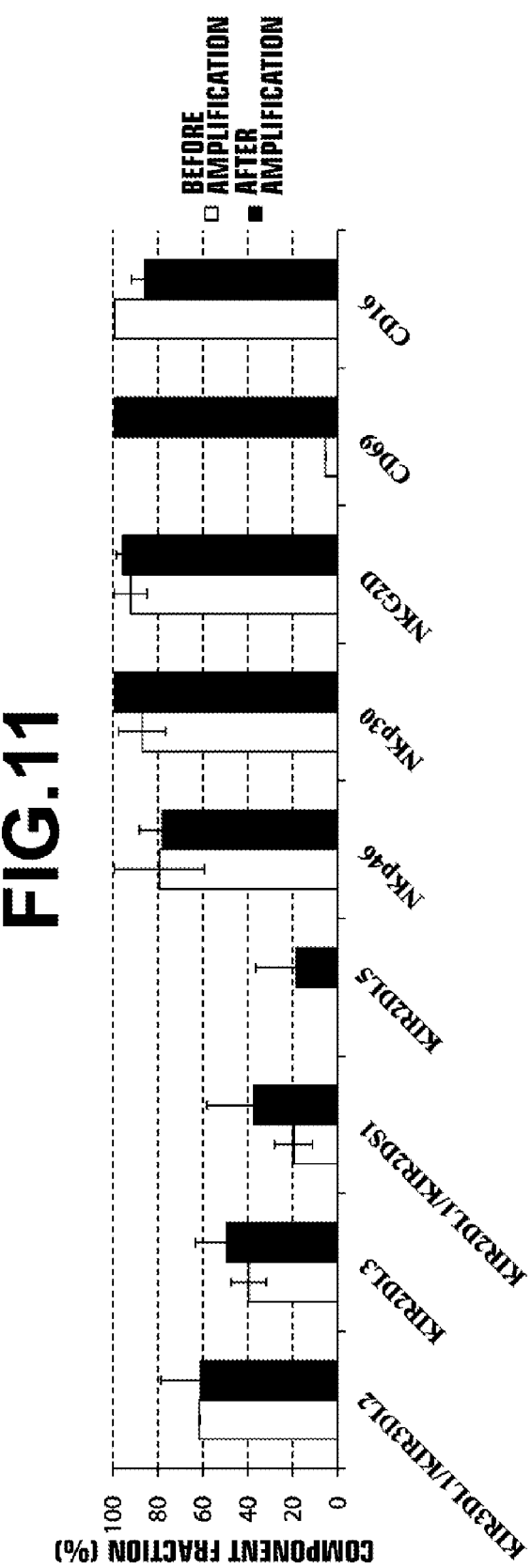
FIG. 11 is a graph comparing results of analysis with various cell surface markers.

FIGS. 7, 9 and 11 show graphs comparing flow cytometry analysis results of cell surface markers. FIGS. 8 and 10 show graphs of mean fluorescent intensity (MFI) measurements of CD69 and CD16. The standard error of each experimental condition was calculated from the number of cells of the three experiments carried out under identical conditions. As clearly demonstrated by FIGS. 7 to 11, the cells amplified by the method of the present invention have stronger expression of CD69, KIR2DL3, KIR2DL1/KIR2DS1, KIR2DL5, NKp30, and NKG2D compared with the cells before amplification. Especially, expression of CD69 in the amplified cells was about 100%. As clearly demonstrated by these figures, the cells prepared by the method of the present invention express differentiation markers of NK cells. It was suggested that the NK cells have high cytotoxic activity.

The experimental results of this Example demonstrate that by cultivating in the KBM medium after removal of CD3-positive cells, that is, T cells, nearly exclusive amplification of NK cells can be carried out selectively and efficiently. It was suggested that a large number of NK cells can be prepared not only from healthy volunteers but also from patients suffering from cancer, infectious diseases, and other disease conditions. It was also suggested that the method of the present invention can remarkably amplify not only NK cells derived from peripheral blood, but also cells derived from other tissues and organs, especially, NK cells derived from umbilical cord blood.

Example 2

Amplification of NK cells (2)

1. Materials and Methods

NK cells were prepared from healthy volunteers according to the method described in connection with Example 1. Cell-Gro SCGM (2001 CellGenix GmbH, Iwai Chemicals Company) supplemented with 2500 IU/mL of IL-2 (AF-200-02-2. Peprotech, Toyobo Co., Ltd.) and 5% of self serum (referred to as "CellGro medium") was prepared as a cell culture medium. The NK cells were amplified in the KBM and Cell-Gro media according to the method described in connection with Example 1.

2. Results

Figure 12:
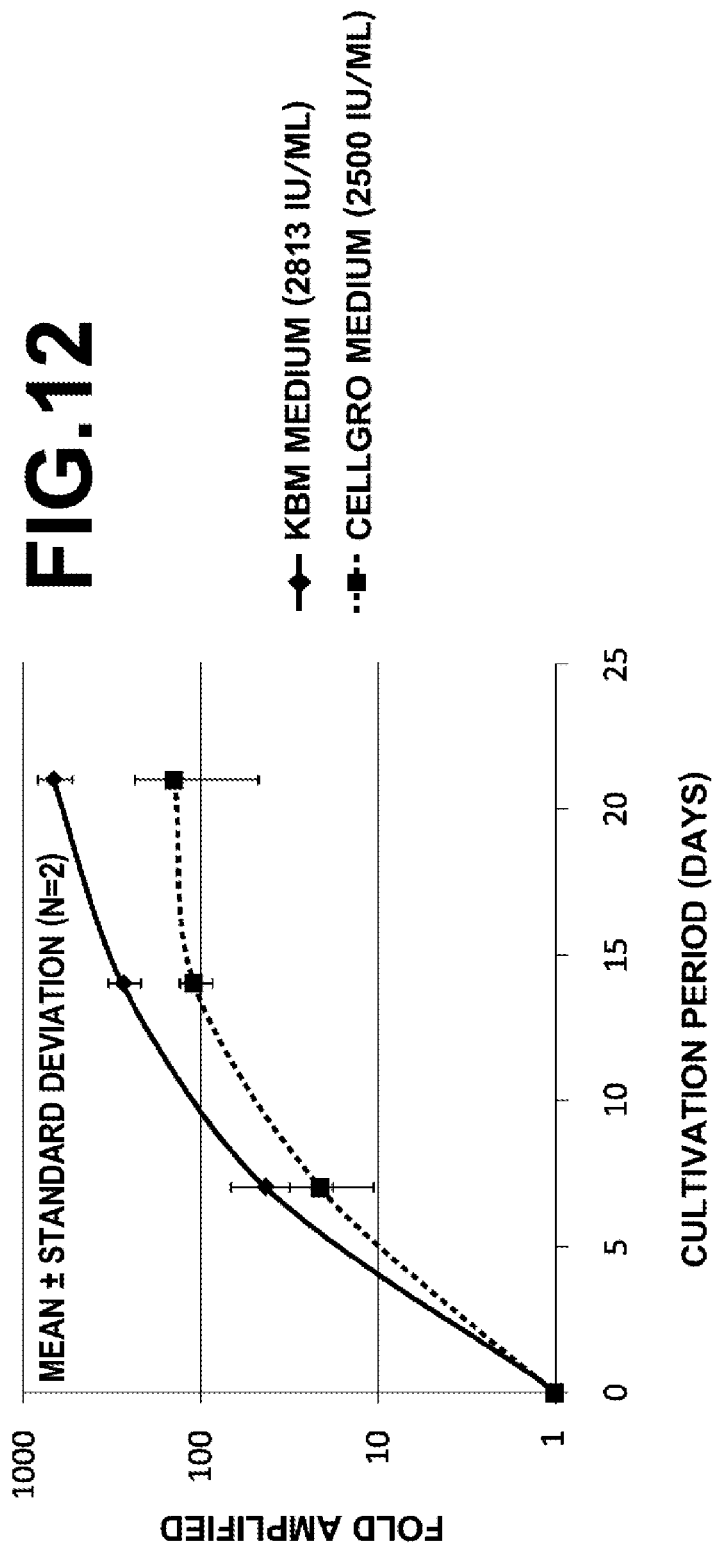
FIG. 12 is a graph illustrating growth curves of NK cells cultured in KBM and CellGro media, as calculated in multiplicity of amplification.

FIG. 12 is a graph illustrating growth curves of NK cells cultured in KBM and CellGro media, as calculated in multiplicity of amplification. The multiplicity of amplification was calculated by dividing the number of NK cells on Days 7, 14 and 21 by the number of NK cells at the start of cultivation. The standard error of each experimental condition was calculated from the number of cells of the two experiments carried out under identical conditions. The multiplicity of amplification of NK cells in KBM and CellGro media kept increasing until Day 21. The multiplicity of amplification on Day 21 was about 670 fold in the KBM medium and about 140 fold in the CellGro medium.

The experimental results of this Example demonstrated that NK cells are sufficiently amplified in the KBM and CellGro media. Therefore, it was suggested that NK cells can be amplified in a medium comprising 2500-2813 IU/mL of IL-2, irrespective of the type of cell culture medium.

Example 3

1. Materials and Methods (1) Quantitative Evaluation of Cytotoxic Activity

NK cells were prepared according to the method described in connection with Example 1 and used as effector cells. K562 cells (chronic myeloid leukemia cells) were prepared according to a method commonly known by those skilled in the art, and used as target cells. The cytotoxic activity of amplified NK cells and NK cells which had not been amplified (referred to as "non-amplified NK cells") were quantitatively evaluated according to a method commonly known by those skilled in the art. Briefly, the target cells were labeled by cultivating for 10 minutes in RPMI-1640 medium supplemented with 3,3'-dioctadecyloxacarbocyanine (D4292, Sigma-Aldrich Japan K.K.) at a final concentration of 0.01 mM. After labeling, the target cells were washed three times with PBS (−) and a serum-free IMDM medium. The effector cells and the target cells were inoculated in a round-bottom 96-well culture plate and co-cultured for 2 hours in the serum-free IMDM medium. The ratio of effector cell to target cell (E:T ratio) was set at 3:1, 2:1, 1:1, 1:5 and 1:10. The cytotoxic activity (%) was quantitatively determined by flow cytometry with an anti-MHC class I antibody (311409, BioLegend Japan KK) and 7-aminoactinomycin D (A9400, Sigma-Aldrich Japan K.K.).

(2) Expression of Differentiation Markers of NK cells

NK cells were amplified according to the method described in connection with Example 1. The NK cells at the start of cultivation and on Days 3, 7, 14 and 21 were co-cultured with K562 cells at an E:T ratio of 2:1 for 2 hours. Then, component fraction of CD107a-positive cells in the NK cells were analyzed by flow cytometry with an anti-CD107a antibody (328606, BioLegend Japan KK).

(1) Quantitative Evaluation of Cytotoxic Activity

Figure 13:
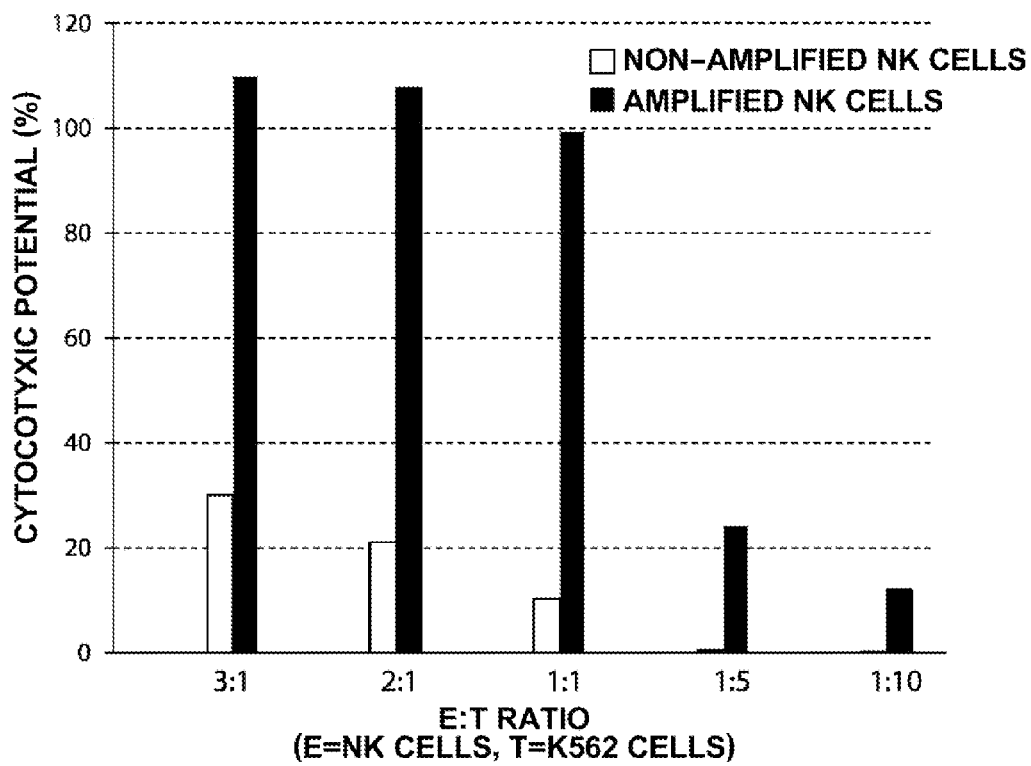
FIG. 13 is a graph illustrating result of cytotoxic activity against K562 cells of NK cells derived from peripheral blood and amplified according to the method of the present invention.

FIG. 13 is a graph illustrating result of cytotoxic activity against K562 cells of NK cells derived from peripheral blood and amplified according to the method of the present invention. The ordinate of the graph represents cytotoxic activity (unit: %). The open bars represent cytotoxic activities of non-amplified NK cells and the closed bars represent cytotoxic activities of amplified NK cells. The abscissa represents E:T ratios of amplified or non-amplified NK cells and K562 cells. At an E:T ratio of 3:1, the cytotoxic activity was about 30% for non-amplified NK cells and about 110% for amplified NK cells. At an E:T ratio of 2:1, the cytotoxic activity was about 20% for non-amplified NK cells and about 107% for amplified NK cells. At an E:T ratio of 1:1, the cytotoxic activity was about 10% for non-amplified NK cells and about 100% for amplified NK cells. At E:T ratios of 1:5 and 1:10, the cytotoxic activity of amplified NK cells was about 25% and about 15%, respectively.

Figure 14:
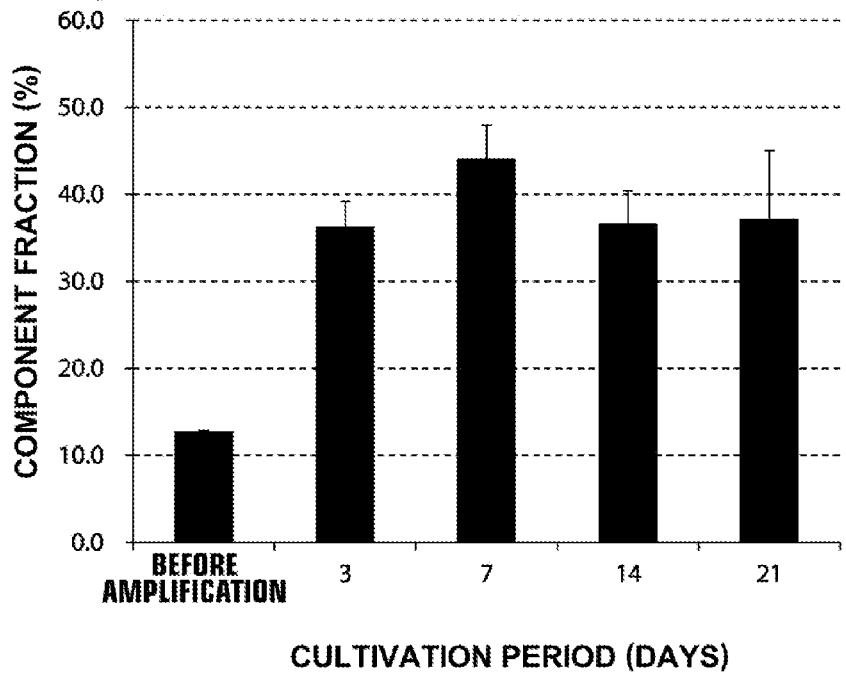
FIG. 14 is a graph illustrating temporal changes of component fraction of CD107a-positive cells, as determined by flow cytometry relative to total cultured cells.

FIG. 14 is a graph illustrating temporal changes of component fraction of CD107a-positive cells, as determined by flow cytometry relative to the total number of cultured cells. The standard error of each experimental condition was calculated from the number of cells of the five experiments carried out under identical conditions. "Component fraction of CD107a-positive cells" represents a percentage ratio of CD107a-positive cells relative to the entirety of cultured cells in each experimental group. In the graph of FIG. 14, the ordinate represents component fractions (%) of CD107a-positive cells relative to the entirety of cultured cells and the abscissa represents days of the cultivation period. The component fraction of CD107a-positive cells increased about 35% from the start of cultivation to Day 3 and the component fraction was maintained until Day 21.

The experimental results of this Example demonstrate that the NK cells amplified according to the present invention have high cytotoxic activity. Thus, it was demonstrated that the present invention can selectively and efficiently amplify NK cells with high cytotoxic activity without using feeder cells, NK cells transfected with foreign molecules, or the like. Additionally, it was suggested that the cytotoxic activity will be high when the NK cells are amplified not only from cells of peripheral blood origin but also from cells of other tissue or organ origin, especially from cells of umbilical cord blood origin.

Example 4

Amplification of NK cells (3) (Repeated Removal of CD3-Positive Cells)

After the experiments described in connection with Examples 1 to 3, while carrying out further experiments of amplifying NK cells, it was found that the component fraction of CD3-positive cells relative to the entirety of culture cells may exceed 30%, as in the result of this Example, as the CD3-positive cells increased non-selectively. The frequency of this non-selective increase of CD3-positive cells was about 30% of experiments in which NK cells were amplified from peripheral blood mononuclear cells collected by apheresis from patients of advanced cancer (data not shown). Therefore, in order to amplify NK cells selectively, the inventors of the present invention tried to carry out the step of removing CD3-positive cells more than once.

1. Materials and Methods

NK cells were amplified and the number of cells and cell surface markers were analyzed according to the method described in connection with Example 1. The mononuclear cell suspensions were prepared from patients of advanced cancer (oral cancer, gall bladder cancer and bile duct cancer). Removal of CD3-positive cells was carried out once or twice. The CD3-negative cells were cultivated for 14 days in the KBM medium.

2. Results

FIG. 15 is a bar graph illustrating component fractions of NK cells (CD3-negative/CD56-positive) relative to the total number of cultured cells after removing CD3-positive cells once and twice. The error bar of each experimental condition represents standard error of the measured values of experimental results repeated three times under identical conditions. The component fractions of NK cells, CD3-positive cells and other cells represent percentage ratios of NK cells, CD3-positive cells and other cells relative to the entirety of culture cells of each experimental group. The ordinate of the graph represents component fractions (%) of NK cells, CD3-positive cells and other cells relative to the entirety of cultured cells and the abscissa represents times to carry out the step of removing CD3-positive cells. The component fraction (%) of NK cells relative to the entirety of culture cells was about 50% when CD3-positive cells were removed once, and about 65% when CD3-positive cells were removed twice.

The experimental results of this Example demonstrate that repeated removal of CD3-positive cells reduces the component fraction of CD3-positive cells relative to the entirety of culture cells, and increases the component fraction of NK cells relative to the entirety of culture cells. The repeated removal of CD3-positive cells, however, is not sufficient to amplify NK cells selectively. Therefore, the inventors of the present invention tried to combine a treatment other than the repeated removal of CD3-positive cells.

Example 5

Amplification of NK cells (4) (Removal of CD3-positive cells and CD34-positive cells)

1. Materials and Methods

NK cells were amplified and cell number and cell surface markers were analyzed according to the method described in connection with Example 1. Mononuclear cell suspensions were prepared from patients of advanced cancer (oral cancer, gal bladder cancer and bile duct cancer). After CD3-positive cells were removed, hematopoietic progenitor cells were removed. The removal of the hematopoietic progenitor cells was carried out by removing cells expressing CD34 on the cell surfaces thereof (CD34-positive cells) with a biotinylated anti-CD34 antibody (343523, BioLegend Japan KK) and magnetic beads (Dynabeads biotin binder, 110-47, Life Technologies Japan Ltd.). Briefly, the CD34-positive cells were reacted with the biotinylated anti-CD34 antibody. Afterwards, centrifugation was carried out to remove the supernatant, and a suspension of cells bound to the above-mentioned antibody was prepared. The magnetic beads were washed once with PBS supplemented with 0.1% of BSA and were added to the suspension at 50 uL per $10^7$ cells. The suspension with the magnetic beads was mixed at 4° C. for 30 minutes using a rotator. The magnetic beads were separated from the suspension with a magnet, removing the CD34-positive cells. The cells remaining in the suspension (referred to as "CD3- and CD34-negative cells") were cultivated for 14 days in the KBM medium. For the flow cytometry, an anti CD34 antibody (343505, BioLegend Japan KK) was additionally used.

Figure 16A:
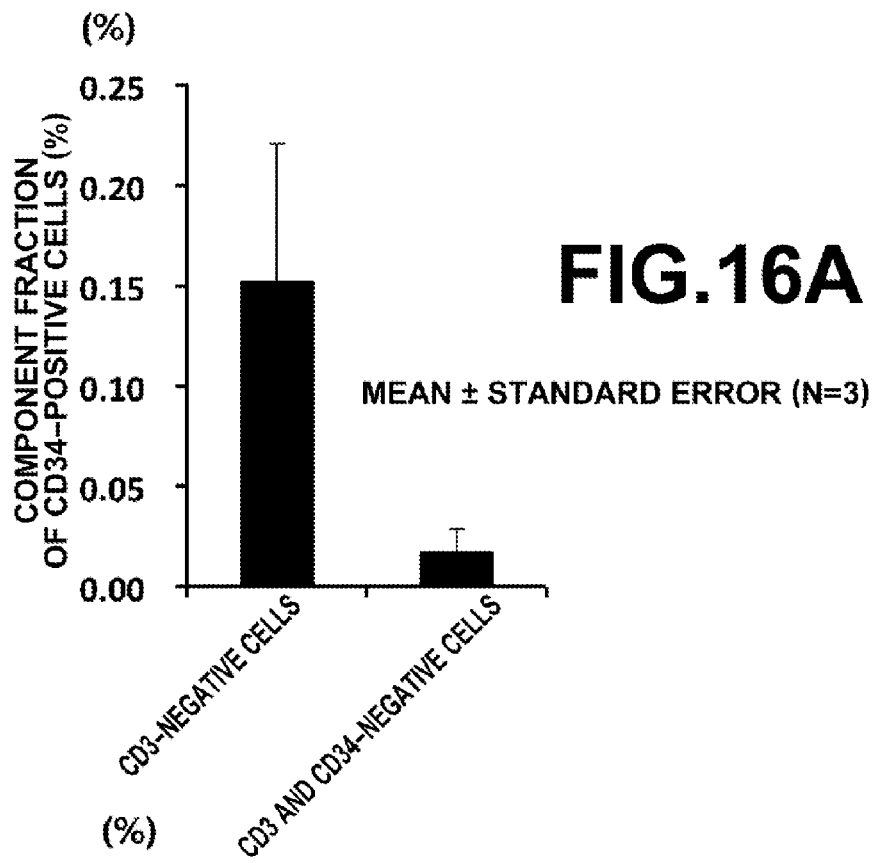
FIG. 16A is a bar graph illustrating component fractions of CD34-positive cells relative to CD3-negative cells and CD3- and CD34-negative cells before amplification.
Figure 16B:
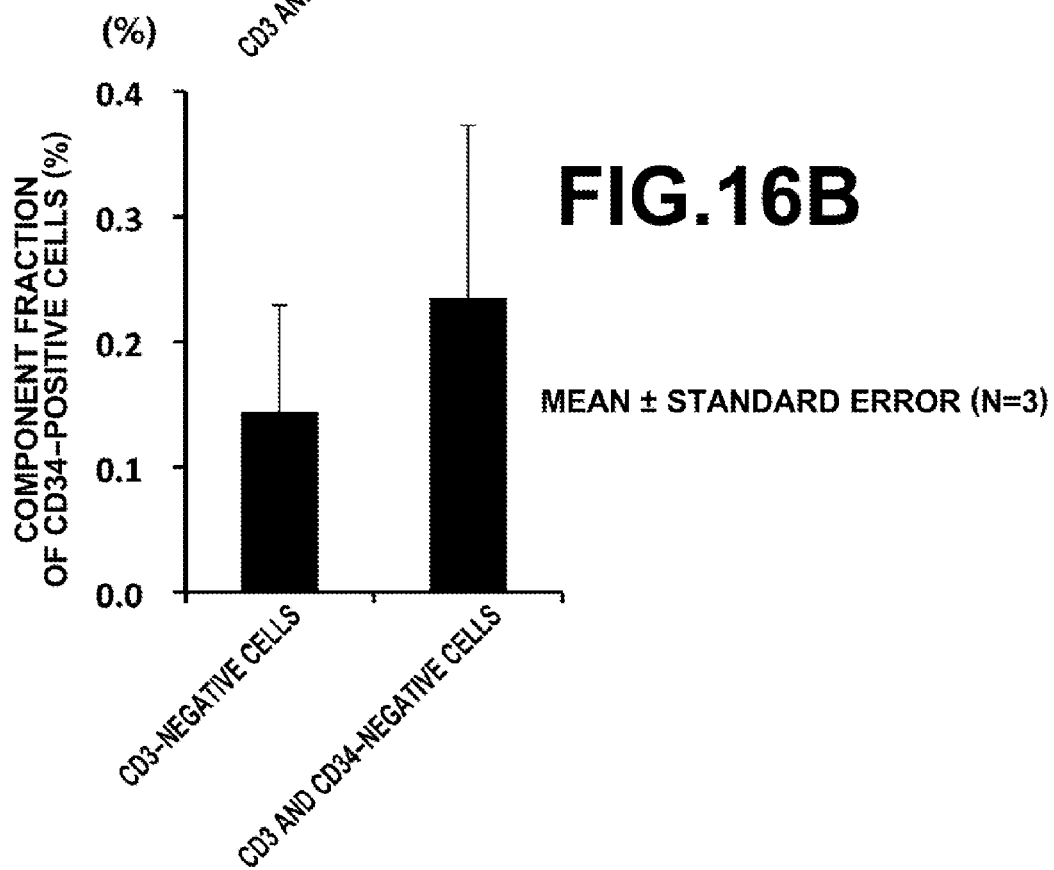
FIG. 16B is a bar graph illustrating component fractions of CD3-positive cells relative to CD3-negative cells and CD3- and CD34-negative cells before amplification.

FIG. 16A is a bar graph illustrating component fractions of CD34-positive cells relative to CD3-negative cells and CD3- and CD34-negative cells before amplification. FIG. 16B is a bar graph illustrating component fractions of CD3-positive cells relative to CD3-negative cells and CD3- and CD34-negative cells before amplification. The error bar of each experimental condition represents standard error of the measured values of experimental results repeated three times under identical conditions. Component fractions of CD34-positive cells and CD3-positive cells represent percentage ratio of CD34-positive cells and CD3-positive cells relative to the entire cultured cells in each experimental group. The ordinate of the graph represents component fractions (%) of CD34-positive cells and CD3-positive cells before amplification relative to the entire cultured cells. The abscissa of the graph represents cell type to be amplified in each experimental group. The component fraction (%) of CD34-positive cells before amplification was about 0.15% in CD3-negative cells and about 0.25% in CD3- and CD34-negative cells.

FIG. 17 is a bar graph illustrating component fractions of NK cells (CD3-negative/CD56-positive) relative to total cultured cells amplified from CD3-negative cells and CD3- and CD34-negative cells. The error bar of each experimental condition represents standard error of the measured values of experimental results repeated three times under identical conditions. Component fractions of NK cells, CD3-positive cells other cells represent percentage ratio of NK cells, CD3-positive cells and other cells relative to the entire cultured cells in each experimental group. The ordinate of the graph represents component fractions (%) of NK cells, CD3-positive cells and other cells relative to the entire cultured cells. The abscissa of the graph represents cell type to be amplified in each experimental group. Component fraction (%) of NK cells after amplification relative to the entire cultured cells was about 60% in CD3-negative cells and about 90% in CD3- and CD34-negative cells.

The experimental results of this Example demonstrate that the component fraction of NK cells (CD3-negative/CD56-positive) relative to the entirety of cultured cells remarkably increases by removing CD3-positive cells and CD34-positive cells. It was also demonstrated that NK cells can be amplified at high purity by removing CD3-positive cells and CD34-positive cells, even when the NK cells are amplified from peripheral blood mononuclear cells collected by apheresis.

CONCLUSION

As clearly understood from the above-mentioned experimental results, it is now possible to prepare a large number of NK cells by removing CD3-positive cells (T cells) from mononuclear cells derived from peripheral blood. As shown in the results of this Example, the cells amplified by the method of the present invention have very high cytotoxic activity. Further, it is now possible to prepare highly purified NK cells by removing CD3-positive cells (T cells) and CD34-positive cells (hematopoietic progenitor cells) from peripheral blood mononuclear cells.

It had been known that, in the conventional methods for amplifying NK cells, the cytotoxic activity of the NK cells is low. For example, Terunuma, H. et al. (Patent Document 1) reported that their NK cells, which were derived from peripheral blood of healthy volunteers, had a purity of 81.2%, 130 fold amplification, and cytotoxic activity of 66% (E:T=3:1). Tanaka, J. et al. (Patent Document 2) reported that their NK cells, which were derived from peripheral blood of healthy volunteers, had a purity of 73.4%, 6268 fold amplification, and cytotoxic activity of about 55% (E:T=1:1). Carlens, S. et al. (Non-patent Document 4) reported that their NK cells, which were derived from peripheral blood of myeloma patients, had a purity of 55%, 193 fold amplification, and cytotoxic activity of 45% (E:T=1:1). Alici, E. et al. (Non-patent Document 5) reported that their NK cells, which were derived from peripheral blood of myeloma patients, had a purity of 65%, 1625 fold amplification, and cytotoxic activity of about 10% (E:T=1:1). Fujisaki, H. et al. (Non-patent Document 6) reported that their NK cells, which were derived from peripheral blood of healthy volunteers, and which were cultivated with genetically modified tumor cells as feeder cells, had a purity of 96.8%, 277 fold amplification, and a maximum cytotoxic activity of about 90% (E:T=1:1). Compared with these results, the amplified NK cells according to the present invention have a purity of about 90%, 400 fold amplification, and cytotoxic activity of about 100% (E:T=1:1). The cytotoxic activity of NK cells obtained by conventional techniques against K562 cells was up to about 90% (E:T=1:1) when the genetically modified tumor cells were used as feeder cells, and 66% (E:T=3:1) when no feeder cells were used. The NK cells of the present invention, in contrast, are amplified without any feeder cells and have the cytotoxic activity of about 100% (E:T=1:1). The present invention is remarkably better than the conventional art, because the NK cells of the present invention have high cytotoxic activity but no risk of contamination of feeder cells in the final product. Accordingly, the present invention is useful for preparing a large number of NK cells with high cytotoxic activity and high purity from collected blood cells.

The invention claimed is:

1. A method for amplifying NK cells, comprising the steps of:
    preparing cell population which is comprised of NK cells;
    removing T cells from the cell population which is comprised of NK cells; and
    after removal of T cells, cultivating the remaining cells without feeder cells in a medium supplemented with 2500 to 2831 IU/mL of IL-2, as the only cytokine.

2. The method according to claim 1, wherein the step of removing T cells is implemented by a step of removing CD3-positive cells.

3. The method according to claim 1, comprising, between the step of preparing and the step of cultivating a step of:
    removing hematopoietic progenitor cells from the cell population.

4. The method according to claim 3, wherein the step of removing hematopoietic progenitor cells from the cell population is implemented by a step of removing CD34-positive cells.

5. The method according to claim 1, wherein the medium comprise self serum of the donor, AB-type serum, and/or serum albumin.

6. The method according to claim 1, wherein the step of preparing cell population which is comprised of NK cells is implemented by a step of separating mononuclear cells from blood cells collected from a subject.

7. The method according to claim 6, wherein the blood cells are collected from peripheral blood, umbilical cord blood, a bone marrow and/or a lymph node.

8. The method according to claim 7, wherein the blood cells are collected from peripheral blood using apheresis.

9. The method according to claim 1, wherein the cell population is prepared from at least one kind of cells selected from a group consisting of:
    hematopoietic stem cells derived from any stem cells selected from a group consisting: embryonic stem cells, adult stem cells and induced pluripotent stem cells (iPS cells);
    hematopoietic stem cells derived from umbilical cord blood;
    hematopoietic stem cells derived from peripheral blood;
    hematopoietic stem cells derived from bone marrow blood;
    umbilical cord blood mononuclear cells; and
    peripheral blood mononuclear cells.

10. A method for adoptive immunotherapy comprising the steps of:
    preparing a cell population which is comprised of NK cells,
    removing T cells from the cell population,
    after removal of T cells, cultivating the remaining cells without feeder cells in a medium supplemented with 2500 to 2831 IU/mL of IL-2, as the only cytokine, and
    transplanting the NK cells which are amplified from the remaining cells to a patient.

11. The method according to claim 10, wherein the step of removing T cells is implemented by a step of removing CD3-positive cells.

12. The method according to claim 10, comprising, between the step of preparing and the step of cultivating, a step of:

removing hematopoietic progenitor cells from the cell population.

13. The method according to claim 12, wherein the step of removing hematopoietic progenitor cells from the cell population is implemented by a step of removing CD34-positive cells.

14. The method according to claim 10, wherein the medium comprise self serum of the donor, AB-type serum, and/or serum albumin.

15. The method according to claim 10, wherein the step of preparing cell population which is comprised of NK cells is implemented by a step of separating mononuclear cells from blood cells collected from a subject.

16. The method according to claim 15, wherein the blood cells are collected from peripheral blood, umbilical cord blood, a bone marrow and/or a lymph node.

17. The method according to claim 16, wherein the blood cells are collected from peripheral blood using apheresis.

18. The method according to claim 10, wherein the cell population is prepared from at least one kind of cells selected from a group consisting of:
   hematopoietic stem cells derived from any stem cells selected from a group consisting: embryonic stem cells, adult stem cells and induced pluripotent stem cells (iPS cells);
   hematopoietic stem cells derived from umbilical cord blood;
   hematopoietic stem cells derived from peripheral blood;
   hematopoietic stem cells derived from bone marrow blood;
   umbilical cord blood mononuclear cells; and
   peripheral blood mononuclear cells.

* * * * *